United States Patent [19]

Papenfuhs et al.

[11] Patent Number: 5,179,230
[45] Date of Patent: Jan. 12, 1993

[54] PROCESS FOR THE PREPARATION OF 2,3,4,5-TETRAFLUOROBENZOIC ACID

[75] Inventors: Theodor Papenfuhs, Frankfurt am Main; Ralf Pfirmann, Griesheim, both of Fed. Rep. of Germany

[73] Assignee: Hoechst Aktiengesellschaft, Frankfurt am Main, Fed. Rep. of Germany

[21] Appl. No.: 872,059

[22] Filed: Apr. 23, 1992

[30] Foreign Application Priority Data

Apr. 25, 1991 [DE] Fed. Rep. of Germany ....... 4113462

[51] Int. Cl.$^5$ ............................................. C07C 63/04
[52] U.S. Cl. .................................................. 562/493
[58] Field of Search ........................................ 562/493

[56] References Cited

U.S. PATENT DOCUMENTS 3,246,009 4/1966 Loev. B .............................. 562/493

FOREIGN PATENT DOCUMENTS 0140482  1/1988 European Pat. Off. .
355774   2/1990 European Pat. Off. .
0218111  7/1990 European Pat. Off. .
0259663  1/1991 European Pat. Off. .
3810093 10/1989 Fed. Rep. of Germany .
2-33660  9/1990 Japan .
2134900  8/1984 United Kingdom .
2146635  4/1985 United Kingdom .

OTHER PUBLICATIONS

Buxton, D. et al. Aust. J. Chem. 39(12) 2013-26 1986.
Ishikawa, N. et al. Nippon Kagaku Kaishi (1) 200-2 1976.
Gerasimova, T. N. et al. Izv. Sib Otd. Akad. Nauk SSSR, Ser. Khim Nauk (6) 54-60 1975.

*Primary Examiner*—Paul J. Killos

[57] ABSTRACT

A process for the preparation of 2,3,4,5,-tetrafluorobenzoic acid of the formula (1)

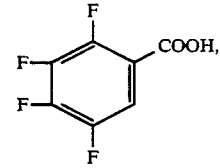

by heating N'-substituted N-aminotetrafluorophthalimides of the formula (2)

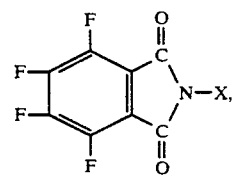

in which X is the radical

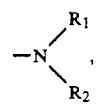

where $R_1$, $R_2$ are a hydrogen atom, an alkyl-$(C_1-C_{10})$-group, aryl group, alkyl-$(C_1-C_6)$-Co- group or aryl-CO- group, it being possible for the aryl or aryl-CO- group in the case of $R_1$ and $R_2$ to be substituted on the aromatic ring by fluorine and/or chlorine atoms and/or alkyl-$(C_1-C_4)$-groups, or $R_1$ and $R_2$ together are a phthaloyl radical which can be substituted on the aromatic ring by 4 chlorine atoms or 4 fluorine atoms, or where X is the radical

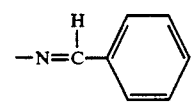

which can be substituted on the aromatic ring by fluorine and/or chlorine atoms and/or alkyl-$(C_1-C_4)$-groups, in an aqueous medium at pH values of approximately −1 to approximately +1 at temperatures of approximately 160 to approximately 220° C.

8 Claims, No Drawings

PROCESS FOR THE PREPARATION OF 2,3,4,5-TETRAFLUOROBENZOIC ACID

The present invention relates to an improved process for the preparation of 2,3,4,5-tetrafluorobenzoic acid from N'-substituted N-amino-3,4,5,6-tetrafluorophthalimides which can be converted into 2,3,4,5-tetrafluorobenzoic acid, an important intermediate for the preparation of antibacterial agents, by acid hydrolysis (DE-A 3,318,145).

To date, 2,3,4,5-tetrafluorobenzoic acid could be synthesized from tetrachlorophthaloyl chloride (G. G. Yakobson, V. N. Odinkov, N. N. Vorozhtsov, Zh. Obshsh. Khim. 36 (1966), 139; Imperial Chemical Industries PLC, EP 140,482, GB 2,146,635, 24.7.84), from tetrafluoroanthranilic acid (S. Hayashi, N. Ishikawa, Bull. Chem. Soc. Jap. 45 (1972), 2909), from 1,2,3,4,-tetrafluorobenzene (L. J. Belf, M. W. Buxton, J. F. Tilney-Bassett, Tetrahedron 23 (1967), 4719; Z. Naturforsch. 31B (1976), 1667), from tetrachlorophthalic anhydride (Bayer AG, DE 3,810,093 A1, 5.10.89; Warner-Lambert Co., EP 218,111, 9.9.86) or from tetrachlorophthalodinitrile (Imperial Chemical Industries PLC, GB 2,134,900, 22.8.84) via steps which are in some cases complicated and/or cannot be realized industrially. The same holds true for the preparation of 2,3,4,5-tetrafluorobenzoic acid from 1,2,-dibromotetrafluorobenzene (C. Tamborski, E. J. Soloski, J. Organometallic Chem. 10 (1967), 385) and the method described by P. Sartori and A. Golloch (Chem. Ber. 101 (1986), 2004), which starts from tetrafluorophthalic acid. N-carbon-substituted tetrachlorophthalimides were also employed for the synthesis of tetrafluorophthalic acid (SDS Biotech K. K., EP 259,663, 18.8.87), which can be converted into 2,3,4,5-tetrafluorobenzoic acid.

2,3,4,5-tetrafluorobenzoic acid can be obtained from tetrafluorophthalic acid or its anhydride by a variety of processes (EP 194,671; EP 218,111; JP 01/025,737; JP 63/295 529). Some of these processes are carried out with the use of reagents which are not available for industrial production or are ecologically unacceptable. The main problem is mostly the fact that tetrafluorophthalic acid has to be isolated before it is further reacted, which can cause considerable problems.

There was therefore a demand for a better preparation method for 2,3,4,5-tetrafluorobenzoic acid, which could be satisfied by the process according to the invention.

The present invention relates to an improved process for the preparation of 2,3,4,5-tetrafluorobenzoic acid of the formula (1)

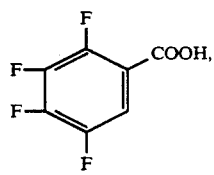

by heating N'-substituted N-aminotetrafluorophthalimides of the formula (2)

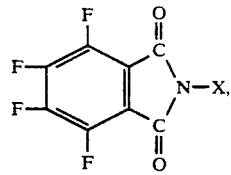

in which X is the radical

where $R_1$, $R_2$ are in each case a hydrogen atom, an alkyl-$(C_1-C_{10})$- group, aryl group, for example the phenyl group, an alkyl-$(C_1-C_6)$-CO- group, for example the acetyl group, an aryl-CO- group, for example the benzoyl group, where the aryl or aryl-CO- groups in the case of $R_1$ and $R_2$ can be substituted on the aromatic ring for example by fluorine and/or chlorine atoms and/or alkyl-$(C_1-C_4)$-groups, or $R_1$ and $R_2$ together are a phthaloyl radical which can be substituted on the aromatic ring by 4 chlorine atoms or 4 fluorine atoms, preferably the radical

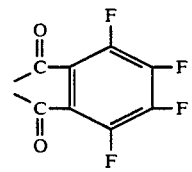

or in which X is the radical

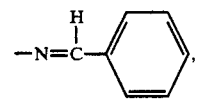

which can be substituted on the aromatic ring for example by fluorine and/or chlorine atoms and/or alkyl-$(C_1-C_4)$-groups, in an aqueous medium at pH values of approximately −1 to approximately +1, preferably approximately −0.2 to approximately +0.4, at temperatures of approximately 160° to approximately 220° C., preferably approximately 190° to approximately 205° C., in a closed vessel (reactor).

The reaction mixture can be brought to the desired acidic pH either using organic acids such as, for example, trifluoroacetic acid, alkylsulfonic or arylsulfonic acids such as, for example, methanesulfonic acid, trifluoromethanesulfonic acid, hexafluoropropanesulfonic acid or p-toluenesulfonic acid, or using inorganic mineral acids such as, for example, hydrochloric acid, hydrobromic acid, hydriodic acid, sulfuric acid, chlorosulfonic acid or phosphoric acid.

The 1-step process according to the invention has the advantage that intermediate isolation of tetrafluorophthalic anhydride or of tetrafluorophthalic acid, which causes considerable problems in some cases, depending on the process, can be dispensed with. In contrast, 2,3,4,5-tetrafluorobenzoic acid is only sparingly soluble in aqueous media and can be obtained as crude product by filtration.

Since carbon dioxide is formed as reaction gas in this reaction, the pressure prevailing on carrying out the process depends on the level to which the vessel (reactor) is filled, the solubility of carbon dioxide in the reaction medium at the particular reaction temperature, and on the real behavior of the gas. However, it is always at least as high as the vapor pressure of the reaction temperature, i.e. pressure between approximately 6.1 bar (160° C.) and approximately 22.9 bar (220° C.)

To prevent corrosion on the apparatus used by free fluoride which is formed during the reaction and which exists in the form of hydrogen fluoride at low pH values, the process can be carried out in the presence of fluoride-scavenging agents. Agents which can be used are calcium salts and silicon dioxide, preferably silicon dioxide having a large internal surface. It is also possible to use trialkyl-($C_2$–$C_6$)tin chlorides, which give polymeric trialkyltin fluorides with fluorides. The following substances are preferably used: calcium salts such as calcium hydroxide, which exists under the reaction conditions in the form of the salt of the acid used, calcium sulfate, calcium carbonate and calcium chloride, and also silicon dioxide with a large internal surface (®Aerosil).

Surprisingly, the 2,3,4,5-tetrafluorobenzoic acid which can be obtained according to the invention can be purified without substantial problems (sublimation) by simple fractionation, this step always having been carried out previously by crystallization from a range of solvents, according to the literature cited further above. 2,3,4,5-tetrafluorobenzoic acid distills over at 99° to 101° C. (1 mbar) in the form of a colorless liquid which immediately solidifies in the receiving vessel (solidification point 83.1° C.). In this manner, the purities required for the potential use of the abovementioned acid (>99.9%) is obtained without problems.

The N'-substituted N-aminotetrafluorophthalimides which are employed as starting compounds of said formula (2) in the process according to the invention can be prepared by reacting 1 mol of 3,4,5,6-tetrachlorophthalic anhydride with at least the equimolar amount, expediently a molar excess of up to approximately 20 mol %, of a nitrogen compound of the formula (2)

(2)

in which $R_1$ and $R_2$ have the abovementioned meanings, in aqueous/alcoholic medium, in glacial acetic acid, in approximately 90 to 100% strength sulfuric acid or in oleum at temperatures (depending on the medium used) of approximately 100° to 220° C. to give the corresponding N'-substituted N-amino-3,4,5,6-tetrachlorophthalimide of the formula (3)

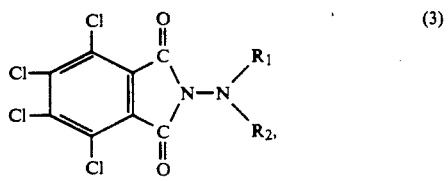
(3)

in which $R_1$ and $R_2$ have the abovementioned meanings, and reacting the resulting imide of the abovementioned formula (3) with potassium fluoride, rubidium fluoride or cesium fluoride or mixtures of these at temperatures of approximately 50° to approximately 230° C., preferably approximately 90° to approximately 140° C., in the presence or absence of a phase transfer catalyst (Halex reaction) in a polar aprotic solvent, either directly or after previous reaction with at least the equimolar amount of benzaldehyde which can be substituted on the aromatic ring for example by fluorine and/or chlorine atoms and/or alkyl-($C_1$–$C_4$)- groups, in a manner known per se to give the corresponding benzyl compound, or after previous acylation with an alkyl-($C_1$–$C_6$)-CO- halide, preferably alkyl-($C_1$–$C_6$)-CO-chloride, carboxylic anhydride of the formula alkyl(-$C_1$–$C_6$)-CO-O-OC-($C_1$–$C_6$)alkyl, an aryl-CO-halide, preferably aryl-CO- chloride, or phthalic anhydride which can be substituted on the aromatic ring by 4 chlorine atoms or 4 fluorine atoms, in a manner known per se.

Suitable polar aprotic solvents for the fluorination (Halex reaction) are, for example, dimethylformamide, dimethylacetamide, dimethyl sulfoxide, tetramethylene sulfoxide, dimethyl sulfone, diphenyl sulfoxide, diphenyl sulfone, sulfolane, N-methylpyrrolidone or 1,3-dimethyl-imidazolidine-2-one.

Phase transfer catalysts which can be used are, for example, quaternary ammonium or phosphonium salts. Suitable compounds which may be mentioned individually are the following: tetraalkyl-($C_1$–$C_{18}$)-ammonium chlorides or tetraalkyl-($C_1$–$C_{18}$)-ammonium bromides, tetraalkyl-($C_1$–$C_{18}$)-phosphoniumchlorides or tetraalkyl-($Cx_1$–$C_{18}$)-phosphonium bromides, tetraphenylphosphonium chloride or tetraphenylphosphonium bromide, [(phenyl)$_m$(alkyl-($C_1$–$C_{18}$))$_n$]-phosphonium chlorides or [(phenyl)$_m$(alkyl-($C_1$–$C_{18}$))$_n$]-phosphonium bromides, where m is 1 to 3, n is 3 to 1 and m+n is 4.

The examples which follow illustrate the process according to the invention in greater detail without imposing any limitations.

EXAMPLE 1

8.72 g (20 mmol) of octafluorobisphthalimide were suspended in 100 ml of water, and the pH of the solution was brought to 0 using concentrated sulfuric acid. The suspension was heated under pressure for 36 hours at 205° C. After cooling, a suspension was obtained. Filtration gave 3.42 g (17.6 mmol) of 2,3,4,5-tetrafluorobenzoic acid as a pale brown solid. Extraction of the aqueous phase with methyl tertbutyl ether, drying the extract over MgSO$_4$, filtration and removal of the solvent, gave a further 3.3 g (17 mmol) of 2,3,4,5-tetrafluorobenzoic acid (total yield, crude, 86%). The crude product from several such batches were combined and subjected to fractional distillation, 2,3,4,5-tetrafluorobenzoic acid distilling over at 99°-101° C. (1 mbar).

Melting point 85.3° C.

$^1$H NMR (CDCl$_3$, internal standard TMS): δ=7.69 (dddd, 1H) $^{19}$F NMR (CDCl$_3$, internal standard CFCl$_3$): δ=−133.2 (dddd, 1F, J=6.1 Hz, 10.4 Hz, 13.3 Hz, 19.9 Hz), −137.8 (dddd, 1F, J=3.3 Hz, 10.5 Hz, 13.1 Hz, 20.9 Hz), −145.6 (dddd, 1F, J=8.4 Hz, 10.5 Hz, 19.6 Hz, 20.9 Hz), −153.5 (dddd, 1F, J=2.7 Hz, 2.7 Hz, 19.6 Hz, 19.9 Hz).

$^{13}$C NMR (CDCl$_3$, internal standard TMS): δ=141.6 (dddd), 144.4 (dddd), 146.7 (dddd), 148.8 (dddd), 167.0 (-COOH)(C-COOH not visible).

MS: m/z(%)=45(12), 75(9), 80(14), 99(54), 119(5), 130(12), 149(57), 177(100), 194(M+,82).

EXAMPLE 2

6.44 g (20 mmol) of N,(N'-benzylidene)-aminotetrafluorophthalimide in aqueous suspension were treated with 85 percent strength phosphoric acid until a pH of approximately −0.5 had been reached, and subsequently kept in this mixture for 25 hours at 210° C. After cooling, the mixture was extracted with methyl tert.butyl ether, the organic phase was washed with aqueous sodium hydroxide solution and discarded (removal of benzaldehyde). The aqueous solution was acidified and reextracted by means of methyl tert.-butyl ether, which gave, after drying and removal of the solvent, 3.23 g (16.6 mmol/83%) of 2,3,4,5-tetrafluorobenzoic acid which can be purified further as described in Example 1.

EXAMPLE 3

5.24 g (20 mmol) of N',N-dimethylaminotetrafluorophthalimide in 100 ml of 5 percent strength hydrochloric acid were heated for 48 hours at 190° C. The resulting solution was extracted using methyl tert.-butyl ether and washed with saturated sodium chloride solution. Drying and removal of the solvent gave 3.41 g (17.6 mmol/88%) of 2,3,4,5-tetrafluorobenzoic acid.

The further purification was as described in Example 1.

EXAMPLE 4

A mixture of 13.1 (30 mmol) of octafluorobisphthalimide, 20.4 g of sulfuric acid, 0.75 g of calcium hydroxide in 120 g of water (pH 0.5 at 20° C.) was heated for 21 hours at 180° C. The internal pressure was limited to a maximum of 12 bar. 11.2 g (96%) of crude 2,3,4,5-tetrafluorobenzoic acid, whose content of pure active substance (GC, calibrated) was 83%, corresponding to a yield of 85% of theory, were obtained from the cooled solution by extraction with methyl tert.butyl ether followed by working-up as described in Example 1.

The further purification was as described in Example 1.

We claim:

1. A process for the preparation of 2,3,4,5-tetrafluorobenzoic acid of the formula (1),

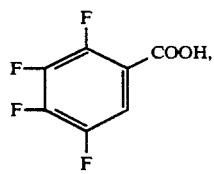

which comprises heating N'-substituted N-aminotetrafluorophthalimides of the formula (2)

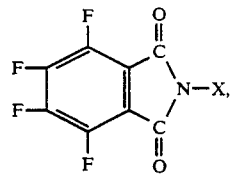

in which X is the radical

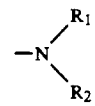

where $R_1$, $R_2$ are hydrogen atom, an alkyl-($C_1$–$C_{10}$)-group, aryl group, alkyl-($C_1$–$C_6$)-CO- group or aryl-CO- group, and when $R_1$ or $R_2$ is the aryl- or aryl-CO- group, said aryl- or aryl-CO- group is optionally substituted on the aromatic ring by fluorine and/or chlorine atoms and/or alkyl-($C_1$–$C_4$)-groups, or $R_1$ and $R_2$ together are a phthaloyl radical which is optionally substituted on the aromatic ring by 4 chlorine atoms or 4 fluorine atoms, or in which X is the radical

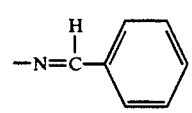

which is optionally substituted on the aromatic ring by fluorine and/or chlorine atoms and/or alkyl-($C_1$–$C_4$)- groups, in an aqueous medium at pH values of approximately −1 to approximately +1 at temperatures of approximately 160° to approximately 220° C.

2. The process as claimed in claim 1, wherein heating is carried out at temperatures of approximately 80° to approximately 205° C.

3. The process as claimed in claim 1, wherein heating is carried out at pH values of approximately −0.2 to approximately +0.4.

4. The process as claimed in claim 1, wherein the pH of the reaction mixture is adjusted using an organic acid, an alkylsulfonic or arylsulfonic acid or an inorganic mineral acid.

5. The process as claimed in claim 1, wherein the 2,3,4,5-tetrafluorobenzoic acid obtained is purified by fractional distillation.

6. The process as claimed in claim 1, wherein the reaction is carried out in the presence of calcium salts, silicon dioxide or trialkyl-($C_2$–$C_6$)tin chlorides.

7. The process as claimed in claim 1, wherein the reaction is carried out in the presence of calcium hydroxide, calcium sulfate, calcium carbonate, calcium chloride or silicon dioxide with a large internal surface.

8. The process as claimed in claim 1, wherein said $R_1$ and $R_2$ together are a said phthaloyl radical, said phthaloyl radical being substituted on the aromatic ring by 4 fluorine radicals and having the formula

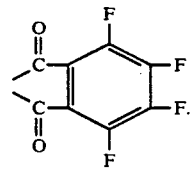

* * * * *